(12) United States Patent
Chen et al.

(10) Patent No.: US 12,562,284 B2
(45) Date of Patent: Feb. 24, 2026

(54) INTELLIGENT EARLY SCREENING MODEL AND CONSTRUCTION METHOD THEREOF FOR ALZHEIMER'S DISEASE

(71) Applicant: Wenzhou Medical University, Wenzhou (CN)

(72) Inventors: Chun Chen, Wenzhou (CN); Qingren Yang, Wenzhou (CN)

(73) Assignee: WENZHOU MEDICAL UNIVERSITY, Wenzhou (CN)

( * ) Notice: Subject to any disclaimer, the term of this patent is extended or adjusted under 35 U.S.C. 154(b) by 435 days.

(21) Appl. No.: 18/140,079

(22) Filed: Apr. 27, 2023

(65) Prior Publication Data

US 2024/0136071 A1 Apr. 25, 2024
US 2024/0233962 A9 Jul. 11, 2024

(30) Foreign Application Priority Data

Oct. 25, 2022 (CN) .......................... 202211312796.5

(51) Int. Cl.
*G16H 50/70* (2018.01)
*G16H 50/50* (2018.01)
(52) U.S. Cl.
CPC ............. *G16H 50/70* (2018.01); *G16H 50/50* (2018.01)
(58) Field of Classification Search
CPC ........ G16H 50/70; G16H 50/50; G16H 50/20; G06N 20/00
See application file for complete search history.

(56) References Cited

U.S. PATENT DOCUMENTS

| | | | |
|---|---|---|---|
| 10,956,212 B1 * | 3/2021 | Andrade-Cetto ... | G06F 16/2282 |
| 2009/0210419 A1 * | 8/2009 | Chitnis ................ | G06F 16/951 |
| 2019/0272922 A1 * | 9/2019 | Albright ................ | G06N 3/04 |
| 2022/0255764 A1 * | 8/2022 | Li ........................ | G06F 21/606 |

(Continued)

OTHER PUBLICATIONS

Christopher M. Florkowski, "Sensitivity, Specificity, Receiver-Operating Characteristic (ROC) Curves and Likelihood Ratios: Communicating the Performance of Diagnostic Tests", Canterbury Health Laboratories, Christchurch, New Zealand, Clin Biochem Rev vol. 29 Suppl (i) Aug. 2008, pp. 83-87, https://pmc.ncbi.nlm.n.*

(Continued)

*Primary Examiner* — Alexander Satanovsky
(74) *Attorney, Agent, or Firm* — WPAT, PC

(57) ABSTRACT

An intelligent early screening model for Alzheimer's disease and a construction method thereof are provided. The construction method includes: retrieving keywords by means of a database to obtain influence factors of the Alzheimer's disease; extracting common feature data of Alzheimer's disease patients from big data in healthcare of a sample region; combining the influence factors and the common feature data, and then inputting into a machine learning model for learning; and verifying and evaluating performance of the machine learning model. The intelligent early screening model for the Alzheimer's disease is constructed through the construction method. The intelligent early screening model can capture Alzheimer's disease high-risk elderly population in common elderly population in advance, realizing early prevention and achieving a goal of eliminating the disease and treating the disease.

5 Claims, 2 Drawing Sheets

(56) References Cited

U.S. PATENT DOCUMENTS

2025/0022579 A1* 1/2025 Schieke ................. G06F 3/048

OTHER PUBLICATIONS

Afshin Gholamy et al., "Why 70/30 or 80/20 Relation Between Training and Testing Sets: A Pedagogical Explanation", University of Texas at El Paso, (2018). Departmental Technical Reports (CS). 1209, 6 pages, https://scholarworks.utep.edu/cs_techrep/1209.*

Afreen Khan et al., "Prospectives of Big Data Analytics and Explainable Machine Learning in Identification of Probable Biomarkers of Alzheimer's disease", Manchester Journal of Artificial Intelligence and Applied Science, vol. 02, No. 01. 2021, Conference Paper • Apr. 2021, pp. 38-44, https://www.researchgate.ne.*

Charlotte James et al., "Performance of Machine Learning Algorithms for Predicting Progression to Dementia in Memory Clinic Patients", JAMA Network Open. 2021;4(12), 11 p., https://jamanetwork.com/journals/jamanetworkopen/fullarticle/2787228.*

\* cited by examiner

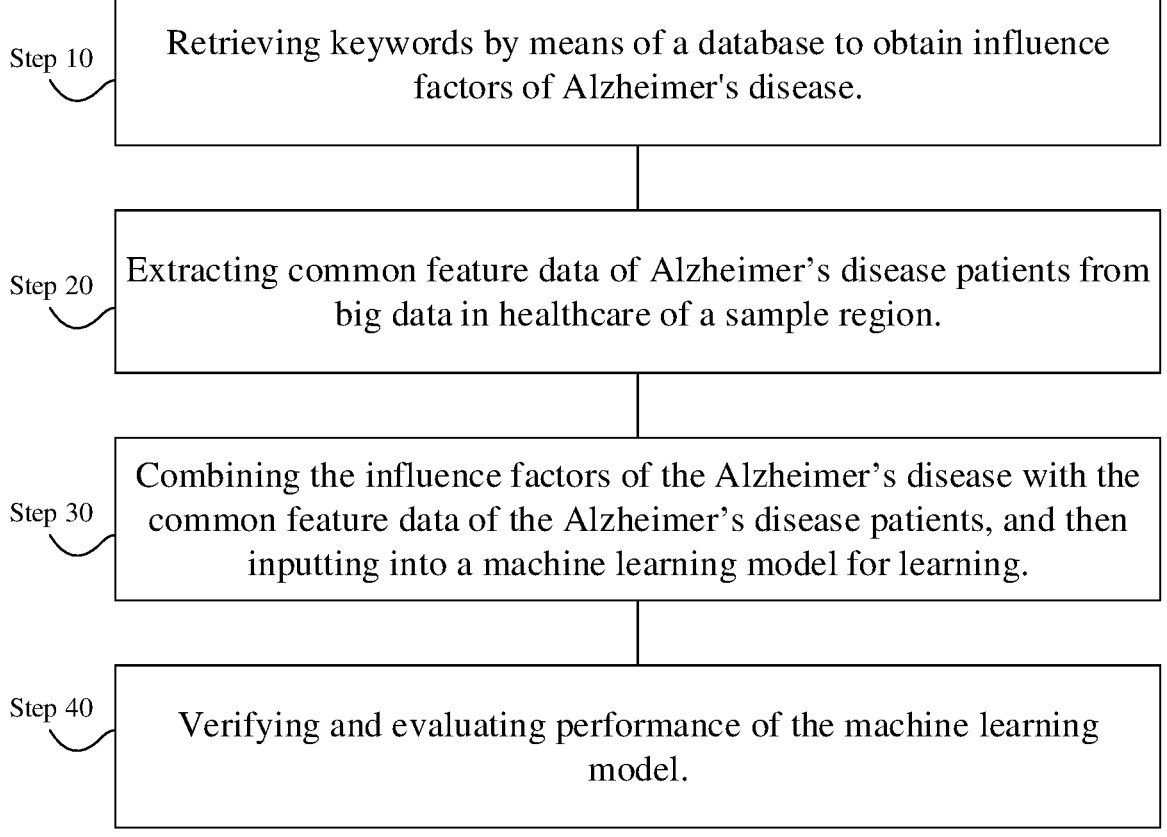

Step 10  Retrieving keywords by means of a database to obtain influence factors of Alzheimer's disease.

Step 20  Extracting common feature data of Alzheimer's disease patients from big data in healthcare of a sample region.

Step 30  Combining the influence factors of the Alzheimer's disease with the common feature data of the Alzheimer's disease patients, and then inputting into a machine learning model for learning.

Step 40  Verifying and evaluating performance of the machine learning model.

FIG. 1

INTELLIGENT EARLY SCREENING MODEL AND CONSTRUCTION METHOD THEREOF FOR ALZHEIMER'S DISEASE

TECHNICAL FIELD

The disclosure relates to the field of biomedicine and health, and more particularly to an intelligent early screening model and its construction method for Alzheimer's disease.

BACKGROUND

Alzheimer's disease (AD) is a neurodegenerative disease with an insidious onset and progressive development. Currently, the common method for screening Alzheimer's disease is to perform periodic examination. It is recommended to have an annual physical examination for individuals aged 60 or above to test their memory and intelligence, which is essential to understand the degree of memory decline of patients every year and can play the role of early detection, diagnosis, and treatment. Another approach is to use modern scientific and technological methods such as cerebrospinal fluid examination for the diagnosis of Alzheimer's disease to achieve early detection and early treatment.

For instance, a Chinese patent document with a publication No. CN113744872A discloses an intelligent interactive Alzheimer's disease auxiliary screening system, including an interactive unit testing module based on voice recognition and an intelligent analysis module based on acknowledged facts, which integrates Montreal cognitive assessment (MoCA) test items, thereby to simplify the testing process.

However, the aforementioned diagnostic methods are only applicable for the diagnosis of already diseased elderly individuals and cannot timely detect the disease, track the disease's entire cycle, and are not suitable for the screening of high-risk elderly individuals in a pre-clinical stage of Alzheimer's disease and a treatment of elderly individuals diagnosed with Alzheimer's disease during the progression of Alzheimer's disease. In this situation, how to perform early detection of high-risk elderly individuals of Alzheimer's disease and effective intervention is a crucial issue for current research.

Therefore, the disclosure aims to solve the technical problem of how to screen Alzheimer's disease as early as possible.

SUMMARY

In response to the shortcomings in the related art, an intelligent early screening model and its construction method for Alzheimer's disease are provided. By analyzing and exploring the most effective screening model for high-risk Alzheimer's disease, the disclosure provides assistance in early detection and effective intervention measures for high-risk populations of Alzheimer's disease, and makes efforts to improve people's health level and quality of life.

To achieve the above objectives, technical solutions of the disclosure are provided as follows.

A method for constructing an intelligent early screening model for Alzheimer's disease, including the following steps:

step 10, retrieving keywords by means of a database to obtain influence factors of the Alzheimer's disease;

step 20, extracting common feature data of Alzheimer's disease patients from big data in healthcare of a sample region;

step 30, combining the influence factors of the Alzheimer's disease with the common feature data of the Alzheimer's disease patients, and then inputting into a machine learning model for learning; and step 40, verifying and evaluating performance of the machine learning model.

In addition, an intelligent early screening model for Alzheimer's disease is also provided, which is obtained by the above mentioned method.

In summary, the above technical solutions have the following beneficial effects. The machine learning model can automatically learn the influence factors of the Alzheimer's disease and the common feature data of the Alzheimer's disease patients, which enables the machine learning model to screen the high-risk populations of Alzheimer's disease. Through the steps of verification and evaluation, the optimal model can be selected, and the constructed machine learning model can achieve accurate screening accuracy. The intelligent early screening model for the Alzheimer's disease obtained through the disclosure can identify high-risk elderly populations of the Alzheimer's disease in ordinary elderly populations in advance, which achieves the shift of prevention before the disease occurs to prevent and treat the disease before it happens.

BRIEF DESCRIPTION OF DRAWINGS

FIG. 1 illustrates a schematic flowchart of a method for constructing an intelligent early screening model for Alzheimer's disease.

DETAILED DESCRIPTION OF EMBODIMENTS

Figure 2:
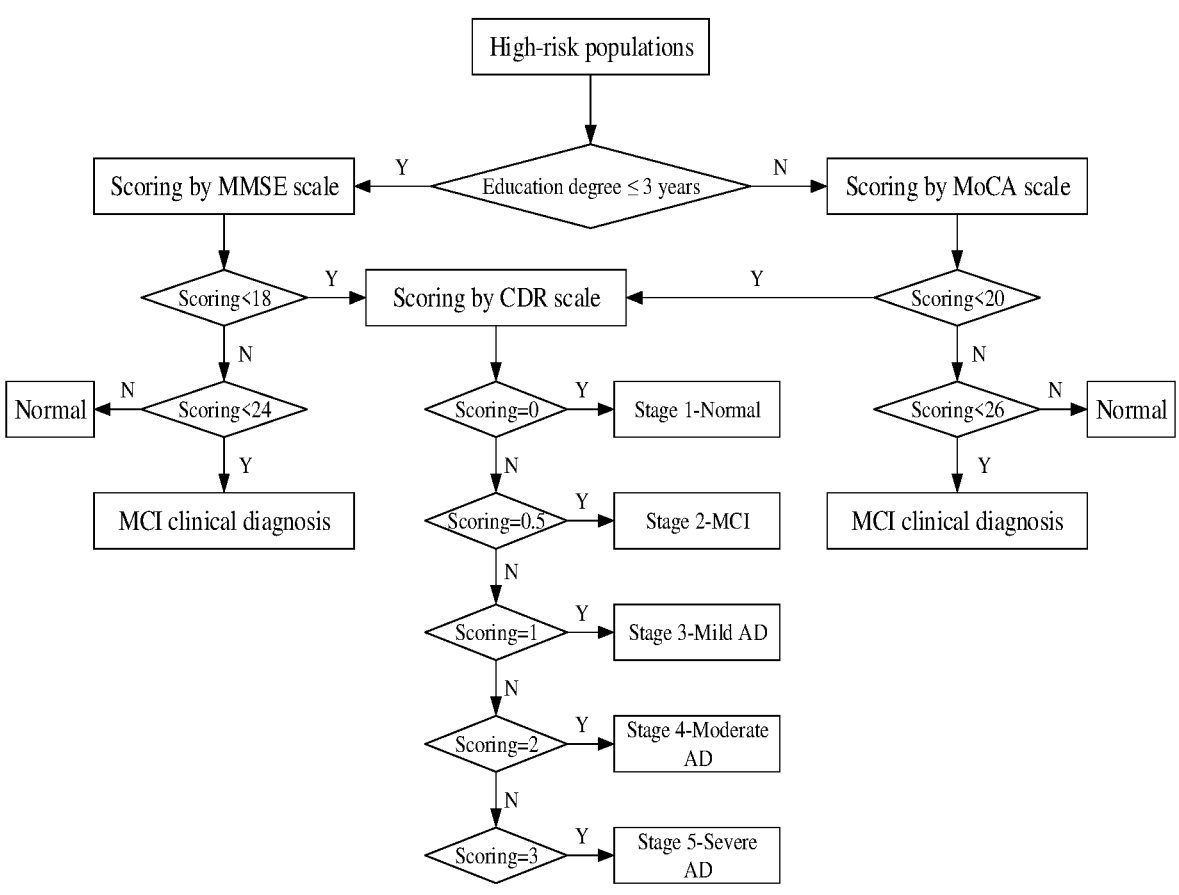
FIG. 2 illustrates a flowchart of determination steps of different stages of the Alzheimer's disease.

Combining with attached drawings and embodiments, the disclosure is further described in detail below.

As shown in FIG. 1, a method for constructing an intelligent early screening model for Alzheimer's disease includes the following steps.

Step 10: keywords are retrieved by means of a database to obtain influence factors of Alzheimer's disease.

The keywords include a keyword "mild cognitive dysfunction" in Chinese, a keyword "mild cognitive impairment" in Chinese, a keyword "mild cognitive impairment" in English, a keyword "MCI" in English, a keyword "cognitive dysfunction" in English, a keyword "senile dementia" in English, and keywords "risk factors" in both Chinese and English. The disclosure retrieves relevant literature by combining the above mentioned keywords in a free manner in various Chinese and English databases such as China National Knowledge Infrastructure (CNKI), Wanfang Web, PubMed, Web of Science, Embase, and Cochrane, thereby to determine the high-risk influence factors of mild cognitive impairment in elderly populations through the literature review. Then, the high-risk influence factors that affect the mild cognitive impairment in the elderly populations are classified into demographic factors, social factors, behavioral factors, disease or physical abnormality factors, and specific genomic biomarker factors.

The influence factors of the Alzheimer's disease include following categories, such as the demographic factors, the social factors, the behavioral factors, the disease or physical abnormality factors, and the specific genomic biomarker factors. The retrieved results are classified according to the above categories, and specially, the influence factors of the Alzheimer's disease are illustrated in Table 1.

Table 1 illustrates the high-risk influence factors of the mild cognitive impairment.

| Category of influence factors | Specific influence factors |
| --- | --- |
| Demographic factors | age, gender, race |
| Social factors | social participation, socioeconomic status, occupation, education degree, alone living, marital status, place of residence |
| Behavioral factors | drinking and dietary habits, smoking, drug abuse, physical activity |
| Disease or physical abnormality factors | infectious diseases: coronavirus disease (COVID-2019), syphilis, acquired immune deficiency syndrome (AIDS)<br>hemorrhagic diseases: elevated antiphospholipid antibodies<br>endocrine, nutritional, and metabolic diseases: hypothyroidism, diabetes, hyperinsulinemia, insulin resistance (IR), hyperlipidemia, hypercholesterolemia, hyperhomocysteinemia, amino acid, lipid, vitamin deficiencies (B12, B6, D, E), folate deficiency, obesity, metabolic syndrome, aluminum intake, sodium intake, lipid metabolism disorders, decreased estrogen levels, insufficient testosterone, lipid peroxidation<br>psychological and behavioral disorders: personality traits, apathy, anxiety, depression, major stress trauma<br>nervous system: leukoaraiosis of brain, hydrocephalus, brain injury, brain tumor, demyelinating disease, acute disseminated encephalomyelitis central nervous system inflammatory syndrome, hippocampus, entorhinal cortex volume, sleep disorders, etc.<br>sensory system: hearing impairment, visual impairment, olfactory degradation, and other sensory impairments<br>circulatory system: transient ischemic attack, cerebral apoplexy, cerebral hemorrhage, cerebral arterial stenosis, cerebral infarction, and other cerebrovascular diseases, atrial fibrillation, coronary heart disease, chronic heart failure, hypertension, atherosclerosis, increased intima-media thickness of the carotid artery, etc.<br>respiratory system: chronic respiratory diseases<br>skin diseases: psoriasis<br>genitourinary systems: chronic kidney disease, proteinuria, menopause, uremia, increased cystatin C, increased uric acid<br>chromosomal abnormalities: Down syndrome<br>other status: postoperative, post-chemotherapy, fatigue, multiple medications |
| Specific genomic biomarkers | cerebrospinal fluid markers: abnormal $A\beta$-related markers, abnormal Tau protein-related markers<br>hematological markers: abnormal $\beta$-amyloid precursor protein (APP) in blood, abnormal $A\beta$ in blood, Tau protein in blood, serum Klotho, abnormal FGF23 expression levels, glycosylated hemoglobin, adipokines, brain-derived neurotrophic factor, C-reactive protein, hemoglobin levels, high endothelin-1 levels<br>genetic markers: presenilin-1 gene, presenilin-2 gene, amyloid precursor protein gene, apolipoprotein E$\varepsilon$4, APP gene, tumor necrosis factor (TNF)-$\alpha$ gene, single nucleotide |

Step 20, common feature data of Alzheimer's disease patients are extracted from big data in healthcare of a sample region. The big data in healthcare of the sample region are obtained through a national health information system platform based on data masking.

Step 21, the big data in healthcare of the sample region is performed to generate a virtual replication set, and then the common feature data of the Alzheimer's disease patients are extracted from both the big data in healthcare of the sample region and the virtual replication set. Statistical analysis for the feature data is carried out by using software such as SPSS Statistics 26.0 (referred to a world's leading statistical software used to solve business and research problems by means of ad-hoc analysis, hypothesis testing, and predictive analytics) and R 3.6.1 (referred to R-Project for statistical computing), missing indicators of which are filled by using missForest algorithm. Due to an imbalance in the distribution of the Alzheimer's disease patients and non-patients in the big data in healthcare of the sample region, the subsequent statistical analysis is not satisfactory. To overcome this problem, the disclosure applies an oversampling method by generating the virtual replication set from existing minority populations to increase the number of the Alzheimer's disease patients in the big data in healthcare of the sample region. And then, the big data in healthcare of the sample region and the virtual replication set are used as measurement data. The normality of the measurement data is tested by using a Kolmogorov-smirnov teat (KS). The measurement data is expressed as Mean±SD or M ($P_{25}$, $P_{75}$), and a between-group comparison is performed by using a t-test or a Mann-Whitney test (also referred to as Wilcoxon rank sum test). The measurement data is expressed as a proportion in percentage (%), and the between-group comparison is tested by using chi-square ($\chi^2$) test. The indicators possessing a difference between two unpaired groups are included in a lasso regression model to analyze the risk influence factors of the Alzheimer's disease. The selected risk influence factors are then put into the machine learning model for further analysis.

Step 30, the influence factors of the Alzheimer's disease are combined with the common feature data of the Alzheimer's disease patients, and then the influence factors of the Alzheimer's disease and the common feature data of the Alzheimer's disease patients are input into a machine learning model for learning.

The machine learning model is based on a federated learning framework. Since there are many factors that cause the Alzheimer's disease and there are certain regional and population differences, the disclosure chooses the machine learning based on the federated learning framework to extract the common feature data of the Alzheimer's disease patients from the big data in healthcare of the sample region, and thereafter combining with the reviewed the high-risk influence factors of the mild cognitive impairment in the literature to determine the high-risk populations of the Alzheimer's disease.

Step 31, the common feature data are divided into a training set and a testing set in proportion, and the training set is used to construct various machine learning models.

Step 32, Bayesian optimization is used to optimize the various machine learning models.

A construction for the machine learning model adopts Python 3.8.5 and anaconda3 integrated development environment. The disclosure divides the collected common feature data into the training set and the testing set in a ratio of 7:3 according to the needs of various machine learning models. The training set is used for constructing the various machine learning models, and the testing set is used for testing the various machine learning models. Logistic regression, Lasso regression, Decision Tree (DT), random forest (RF), Support Vector Machine (SVM), eXtreme Gradient Boosting (XGB) and Artificial Neural Network (ANN) are constructed by using Scikit-learn package. Furthermore, Bayesian Optimization (BO) in the bayes_opt package is used to optimize parameters of the aforementioned various machine learning models to obtain optimal machine learning models.

Step 40, performance of the machine learning model is verified and evaluated.

Step 41, the various machine learning models are evaluated by using a cross-validation method and the testing set.

Evaluation indicators include an area under a receiver operating characteristic curve (ROC) abbreviated as AUC, sensitivity, specificity, accuracy, positive predictive value, and negative predictive value. Specifically, 5-fold cross validation and the testing set are used to evaluate the model's performance, and the evaluation indicators are classified into seven types, such as AUC, sensitivity, specificity, accuracy, positive predictive value, and negative predictive value. Based on the maximum value of AUC, the optimal models among the seven types are selected. Based on the above, the important influence factors of the Alzheimer's disease and their ranking in the populations are identified to help screen for the high-risk populations of the Alzheimer's disease.

The disclosure provides the intelligent early screening model for the Alzheimer's disease by automatically learning the influence factors of the Alzheimer's disease and the common feature data of the Alzheimer's disease patients through the machine learning model. The machine learning model has the ability to screen for high-risk populations of Alzheimer's disease. By the steps of verifying and evaluating, the optimal model can be selected to achieve a relatively accurate screening accuracy, which can identify high-risk elderly populations of the Alzheimer's disease in the general elderly populations, move the prevention gate forward, and achieve the goal of "eliminating potential risks and treating diseases before they occur". The big data in healthcare of the sample region is obtained through the national health information system platform based on data masking.

In another embodiment of the disclosure, an intelligent early screening model for Alzheimer's disease is provided, which is constructed through the above mentioned construction method.

The disclosure constructs the intelligent early screening model for the Alzheimer's disease through a federated learning framework and a national health information system platform based on data masking to further explore databases such as health records, health examinations, elderly specific projects, hypertension-specific projects, diabetes-specific projects, mental illness-specific projects, and medical business to determine high-risk influence factors for the Alzheimer's disease. Then, based on the high-risk influence factors, potential high-risk populations of the Alzheimer's disease can be identified in advance.

The disclosure uses relevant data from the database to carry out Alzheimer's disease screening for high-risk populations, and embeds the screening results as primary keys into personal health records, providing references for subsequent intervention measures. For populations not yet in the database, if they voluntarily undergo Alzheimer's disease high-risk screening, they can be screened with a single click through personal authorization and backend high-risk factor matching in an application named by ZheLiBan. The high-risk factors and high-risk population markers for Alzheimer's disease will also be embedded in the doctor's end. When an individual seeks medical treatment, the doctor's end will directly prompt them with Alzheimer's disease risk information, shifting Alzheimer's disease from "passive prevention and treatment" to "active intervention".

Based on high-risk population screening, the disclosure uses internationally recognized scales to determine the disease stages of the high-risk populations, such as minimum mental state examination (MMSE), Montreal cognitive assessment (MoCA) and clinical dementia rating (CDR). The steps to determine the disease stages of the high-risk populations are shown in FIG. 2 including Stage 1-Normal, Stage 2-Mild Cognitive Impairment, Stage 3-Mild Alzheimer's disease (AD), Stage 4-Moderate AD, and Stage 5-Severe AD.

The disclosure integrates the multiple scales, including MMSE, MoCA, and CDR, to assist in determining whether the high-risk populations are affected by the AD and their specific disease stage from a non-clinical perspective. Every elderly person identified as a high-risk population of the Alzheimer's disease will be followed up regularly by a family doctor who completes a questionnaire. At the same time, the questionnaire results will also be recorded in the health record and transmitted in real-time to the Municipal Health Information Center for archiving and analysis. Leveraging the work of the previous elderly health database construction, during the scale screening process, the power of village (community) grid personnel will be fully utilized to achieve large-scale questionnaire distribution and data collection to assist in determining the disease stage of Alzheimer's disease.

Based on a previous literature review, the disclosure determines that the MMSE and MoCA scores are significantly correlated with education degree. In combination with the suggestions of clinically experienced doctors with rich theoretical knowledge and practical experience, the disclosure uses 3 years of education as a dividing standard to select different scales to determine the mild cognitive impairment population.

First, based on the personal information of the target populations, their years of education are obtained, and different scales are selected to determine the degree of the mild cognitive impairment in the high-risk populations based on their education degree. If the years of education are less than or equal to 3 years, the MMSE scale is used to evaluate the high-risk populations. The maximum score for the MMSE scale is 30 points, the populations with scores greater than or equal to 24 points are considered normal and the populations with scores less than 24 points are considered as cognitive impairment. Among them, the populations scored with 18-23 points are considered as mild cognitive dysfunction, the populations scored with 10-17 points are considered as moderate cognitive dysfunction, and the populations scored with 0-9 points are considered as cognitive dysfunction. If the years of education are more than 3 years, the MoCA scale is used to assess the high-risk populations. The maximum score for the MoCA scale is 30 points, and the populations are initially classified according to the score. Among them, the populations scored with greater than or equal to 26 are considered as normal, the populations scored with greater than or equal to 20 but less than 26 are considered as mild cognitive impairment, and the populations scored with less than 20 are considered likely to have the Alzheimer's disease.

Based on this, the disclosure further monitors the populations with MMSE scores less than 23 and MoCA scores less than 20 using the CDR scale, and carries out preliminary clinical staging of Alzheimer's disease according to the results of the scale. A score of 0 represents a cognitive impairment population without the Alzheimer's disease, a score of 0.5 represents a possible Alzheimer's disease population, a score of 1 represents a mild Alzheimer's disease population, a score of 2 represents a moderate Alzheimer's disease population, and a score of 3 represents a severe Alzheimer's disease population. Given the limited accuracy of the scales, for the Alzheimer's disease patients screened out by the scales, it is recommended that they undergo further clinical diagnosis and enrich related data such as biological markers to improve the clinical diagnosis accuracy of the Alzheimer's disease.

High-risk and diagnosed populations of the Alzheimer's disease can preliminarily determine their disease stage through self-completed or proxy-completed questionnaires on the personal end. At the same time, for elderly individuals with questionnaire results indicating illness, family doctors can make appointments for them to undergo biomarker tests in combination with magnetic resonance imaging (MRI) and cerebrospinal fluid tests to further improve the accuracy of clinical diagnosis of the Alzheimer's disease. In the doctor's end, doctors will take different measures before diagnosis and treatment based on personal information. If a patient is screened as Alzheimer's disease screening patient (this population has completed scale screening before the visit), they will be directly advised to undergo clinical biological marker tests to further determine the stage of Alzheimer's disease. If a patient is a high-risk population for Alzheimer's disease (this population has not completed scale screening before the visit), doctors/nurses will conduct scale screening for them before diagnosis and treatment, preliminarily determine the disease stage of Alzheimer's disease, and advise elderly individuals with scale results indicating illness to undergo relevant clinical biological marker tests to further determine the disease stage of Alzheimer's disease.

The disclosure has the following advantages. 1. Based on the intelligent early screening model for the Alzheimer's disease, it can identify the high-risk elderly population of Alzheimer's disease in the general elderly population in advance, achieve the shift of the prevention threshold, and achieve the goal of eliminating the disease before it arises and treating the disease before it happens. 2. Through the intelligent early screening model for Alzheimer's disease, the screening accuracy of high-risk population is expected to reach about 72%, reducing the incidence rate by 40% and delaying the onset of the disease by 5 years.

The above are only illustrated embodiments of the disclosure. The scope of protection of the disclosure is not limited to the above embodiments. All of the technical solutions under the idea of the disclosure belong to the scope of protection of the disclosure. It should be noted that for those skilled in the related art, several improvements and refinements that do not depart from the principle of the disclosure fall within the scope of protection of the disclosure.

What is claimed is:

1. A method for constructing an intelligent early screening model for Alzheimer's disease, comprising:

step 10, obtaining influence factors of the Alzheimer's disease by searching a database with keywords;

step 20, extracting common feature data of Alzheimer's disease patients from big data in healthcare of a sample region, comprising:

generating a virtual replication set from the big data in healthcare of the sample region by applying an oversampling method to address an imbalance in a distribution of Alzheimer's disease patients and non-patients; and extracting the common feature data from both the big data in healthcare of the sample region and the virtual replication set;

step 30, combining the influence factors of the Alzheimer's disease with the common feature data of the Alzheimer's disease patients, and then inputting into a machine learning model for learning, comprising:

dividing the common feature data into a training set and a testing set proportionally:

constructing a plurality of candidate machine learning models using the training set; the plurality of candidate machine learning models comprising at least Logistic Regression, Random Forest, Support Vector Machine, eXtreme Gradient Boosting, and Artificial Neural Network; and optimizing hyperparameters of the plurality of candidate machine learning models using Bayesian optimization; and step 40, verifying and evaluating performance of the plurality of candidate machine learning models by using a cross-validation method and the testing set based on evaluation indicators comprising: an area under a receiver operating characteristic curve (ROC), sensitivity, specificity, accuracy, positive predictive value, and negative predictive value, so as to obtain an optimal machine learning model; and wherein the method for constructing the intelligent early screening model for the Alzheimer's disease further comprises:

screening a risk population of the Alzheimer's disease based on the optimal machine learning model; and providing a risk prompt to a physician's terminal when an individual identified as the risk population of the Alzheimer's disease seeks medical treatment.

2. The method for constructing the intelligent early screening model for the Alzheimer's disease according to claim 1, wherein the keywords comprise "mild cognitive dysfunction", "mild cognitive impairment", "MCI", "cognitive dysfunction", "senile dementia", and "risk factors".

3. The method for constructing the intelligent early screening model for the Alzheimer's disease according to claim 1, wherein the influence factors of the Alzheimer's disease comprise demographic factors, social factors, behavioral factors, disease or physical abnormality factors, and specific genomic biomarker factors.

4. The method for constructing the intelligent early screening model for the Alzheimer's disease according to claim 1, wherein the machine learning model is based on a federated learning framework.

5. An intelligent early screening model for Alzheimer's disease, wherein the intelligent early screening model for Alzheimer's disease is constructed by using the method for constructing the intelligent early screening model for the Alzheimer's disease according to claim 1.

\* \* \* \* \*